United States Patent [19]

Conner et al.

[11] 4,342,706
[45] Aug. 3, 1982

[54] BENZENE SULFONATE QUATERNARY AMMONIUM SALTS

[75] Inventors: Donald E. Conner, Clifton; Arnold W. Fogel, Park Ridge, both of N.J.

[73] Assignee: Van Dyk & Company, Inc., Belleville, N.J.

[21] Appl. No.: 185,351

[22] Filed: Sep. 8, 1980

[51] Int. Cl.$^3$ .............................................. C07C 87/30
[52] U.S. Cl. .............................. 260/501.15; 260/401; 560/186
[58] Field of Search .......................... 260/401, 501.15; 560/186

[56] References Cited

U.S. PATENT DOCUMENTS

| | | | |
|---|---|---|---|
| 1,737,458 | 11/1929 | Hartman | 260/401 |
| 4,012,398 | 3/1977 | Conner | 260/404.5 Q |
| 4,228,042 | 10/1980 | Letton | 560/186 |

*Primary Examiner*—John F. Niebling
*Attorney, Agent, or Firm*—L. Chasan

[57] ABSTRACT

Novel compositions of matter consisting of benzene sulfonate quaternary ammonium salts have been found to be possessed of very good antistatic, emollient and substantive properties. They are prepared by reacting the amide or ester with the requisite sulfonate.

3 Claims, No Drawings

BENZENE SULFONATE QUATERNARY AMMONIUM SALTS

FIELD OF THE INVENTION

There is an ever increasing need for improved fiber antistatic conditioning agents for e.g., hair and textiles, which are effective in small quantities without the need for auxiliary materials. This invention provides novel compositions having outstanding properties for the purposes mentioned.

SUMMARY OF THE INVENTION

It has now been found that novel chemicals, benzene sulfonate quaternary ammonium salts, corresponding to the formula

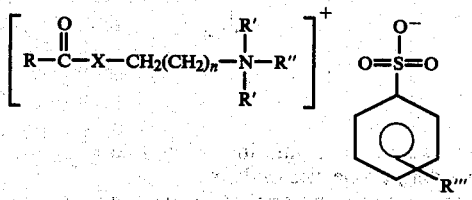

wherein the RCO moiety is selected from the group consisting of gluconic and $C_7$–$C_{21}$ fatty acids; R' is an alkyl group having from 1 to 3 carbon atoms; R'' is an alkyl group having from 1 to 18 carbon atoms; R''' is selected from the group consisting of H and $CH_3$; X is selected from the group consisting of O and NH; and n is an integer of from 1 to 3, have very surprising antistatic, emollient characteristics and are possessed of very good substantivity for many articles, particularly fibers.

DETAILED DESCRIPTION

The chemicals of this invention correspond to the formula shown under Summary of the Invention.

The novel quaternary products of this invention are prepared from the corresponding amide or ester, containing a tertiary nitrogen in the aliphatic portion of the molecule. The amide or ester can also be made directly from available fatty or sugar acids but the triglyceride method is a more desirable commercial one. The acids or oils are reacted with, e.g., a dialkylaminopropylamine or dialkylaminoethanol to obtain the starting amide or ester; see, e.g., U.S. Pat. No. 4,012,398.

The amide or ester containing a tertiary amine group is quaternized by reacting with an ester of benzene or substituted benzene sulfonic acid. This reaction is carried out conveniently in a 40%–50% propylene glycol solution at 90° C.–100° C. for about 6–10 hours.

Sources of the RCO are exemplified by gluconic acid, mink oil fatty acids, safflower fatty acids, hydrogenated tallow fatty acids, corn oil fatty acids, stearic, palmitic, myristic and lauric acids. The sources can be saturated or unsaturated, in the latter case can have up to 3 double bonds, conjugated or unconjugated.

Especially effective compositions are tabulated below:

| $\overset{O}{\underset{\|}{R\,C}}$ | X | n | R' | R'' | R''' |
|---|---|---|---|---|---|
| $\overset{O}{\underset{\|}{CH_3(CH_2)_{16}C}}$ | NH | 2 | $CH_3$ | $C_{18}H_{37}$ | $CH_3$ |
| $\overset{O}{\underset{\|}{HOCH(CHOH)_4C}}$ | NH | 2 | $CH_3$ | $C_{14}H_{29}$ | $CH_3$ |
| $\overset{O}{\underset{\|}{CH_3(CH_2)_{16}C}}$ | O | 1 | $CH_3$ | $C_{18}H_{37}$ | H |

The novel chemicals are liquids to solids, pale yellow to tan and are water-soluble or dispersable.

The compounds of this invention or mixtures thereof can be applied to fibers, e.g. hair or textile, while dissolved or dispersed in suitable volatile liquids, e.g., water, ethyl alcohol, isopropyl alcohol, etc. or mixtures thereof, or other volatile solvents which do not adversely affect the materials.

The solution or dispersion of the active material can contain any suitable amount sufficient to be effective for the purpose stated. Typically, the pure material is present in an amount corresponding from about 0.1 to about 1.0 wt. %, (formula wt. %).

The active ingredient in the consequent carrier can be applied by a variety of means, e.g., spraying, padding, brushing, or otherwise contacting the fibers. The amount of active material of our invention that is present on the dried treated fiber to impart effective antistatic characteristics can be varied but ordinarily it is present in amount by weight corresponding from about 0.05 wt.% to 0.5 wt.% of the dried untreated fiber, usually about 0.1%.

This invention, product workup and properties of the materials will be better understood by reference to the following examples.

EXAMPLE 1

Quaternization of Tallow 3-Dimethylamino Propyl Amide with Stearyl p-Toluene Sulfonate (Composition 1)

Tallow 3-dimethylamino propyl amide 183.8 g, stearyl p-toluene sulfonate 200 g and propylene glycol 255.9 g were heated under nitrogen for 10 hours. An alkali number of 9.8 was obtained. A yield of 640 g of product solution containing propylene glycol was obtained.

Analysis
| | |
|---|---|
| Acid Value | - 10.9 |
| Saponification Value | - 14.6 |
| Alkali Number | - 9.8 |
| pH 1% Solution | - 6.54 |

EXAMPLE 2

Quaternization of Dimethylaminopropyl Gluconamide with Myristyl p-Toluene Sulfonate (Composition 2)

Dimethylaminopropyl gluconamide 279 g, myristyl p-toluene sulfonate 349.6 g and propylene glycol 629 g were reacted at 90° C.–100° C. for 6 hours in a nitrogen atmosphere. A final alkali number of 12.7 was obtained.

A yield of 1,258 g of product solution containing 50% propylene glycol was obtained.

Analysis:
| | |
|---|---|
| Acid Value | - 10.7 |

Saponification Value — 46.1
Alkali Number — 12.7
pH 1% Solution — 8.33

EXAMPLE 3

These compounds are effective hair conditioners and textile anti stats, but several of these compounds have an unexpectedly strong effect at very low concentrations.

In order to test the anti stat properties on textiles, cotton fabric was treated with equal amounts of test compounds of 2 wt.% concentration. Commercial "Downy", a fatty quaternary ammonium chloride fabric softener, was used as a control. A 5 KV positive and a 5 KV negative charge was placed on the fabrics and the decay rate (in seconds) was measured (the faster the rate, the better the compound). From these data in Table I it can be seen that our compounds are much better than "Downy" but compound (1) is very outstanding. The test compounds are identified.

TABLE I
STATIC DECAY MEASUREMENT TEST DATA

| TEST DATA Sample # | Initial Chg. 0 KV Applied | Decay Rate - Seconds Decay Rate @ 5 KV | Decay Rate @ −5 KV |
|---|---|---|---|
| Blank | +200 v | 90.2 | 85.7 |
| Downy | 0 | 79.5 | 72.6 |
| 1 | 0 | 27.3 | 21.97 |
| 2 | 0 | 49.6 | 49.5 |
| 3 | 0 | 68.7 | 64.3 |
| 4 | 0 | 53.7 | 55.4 |
| 5 | 0 | 41.5 | 42.0 |
| 6 | 0 | 48.8 | 47.8 |

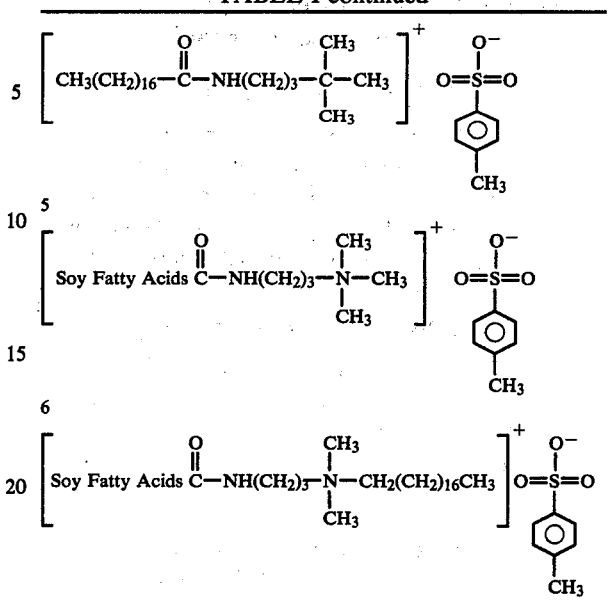

The materials of this invention also demonstrated outstanding properties on hair.

Mixtures of the material of this invention can be employed where desirable.

The advantages of this invention will be apparent to the skilled in the art. Improved flexible antistatic compositions are made available which make it possible to introduce efficiencies through the utilization of small quantities.

It will be understood that this invention is not limited to the specific examples which have been offered as particular embodiments, and that modifications can be made without departing from the spirit thereof.

What is claimed is:

1. As a novel composition of matter, a benzene sulfonate quaternary ammonium salt corresponding to the formula

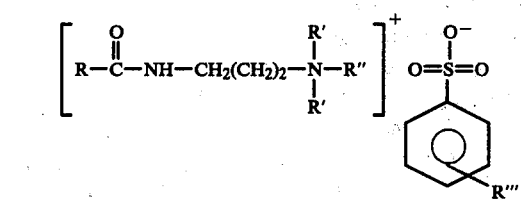

wherein the RCO moiety is from the group consisting of gluconic and $C_7$-$C_{21}$ fatty acid; R' is an alkyl group having from 1 to 3 carbon atoms; R'' is an alkyl group having from 14 to 18 carbon atoms and, R''' is selected from the group consisting of H and $CH_3$.

2. The composition of claim 1 in which the R is $CH_3(CH_2)_{16}$, R' is $CH_3$, R'' is $C_{18}H_{37}$, and R''' is $CH_3$.

3. As a novel composition of matter, a benzene sulfonate quaternary ammonium salt having the formula

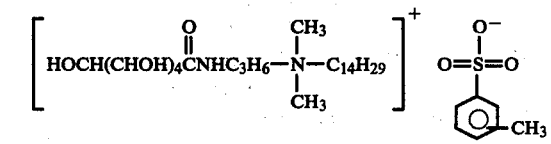

* * * * *